(12) United States Patent
Gonzales et al.

(10) Patent No.: US 9,522,151 B2
(45) Date of Patent: Dec. 20, 2016

(54) DOSING REGIMEN FOR JANUS KINASE (JAK) INHIBITORS

(71) Applicant: Zoetis Services LLC, Florham Park, NJ (US)

(72) Inventors: Andrea J. Gonzales, Kalamazoo, MI (US); Sallie B. Cosgrove, Kalamazoo, MI (US); Phyllis B. Malpas, Kalamazoo, MI (US); Michael Rolf Stegemann, Zaventem (BE); Wendy Turner Collard, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

(21) Appl. No.: 14/415,047

(22) PCT Filed: Jul. 18, 2013

(86) PCT No.: PCT/US2013/051015
§ 371 (c)(1),
(2) Date: Jan. 15, 2015

(87) PCT Pub. No.: WO2014/015107
PCT Pub. Date: Jan. 23, 2014

(65) Prior Publication Data
US 2015/0126535 A1 May 7, 2015

Related U.S. Application Data

(60) Provisional application No. 61/815,803, filed on Apr. 25, 2013, provisional application No. 61/674,289, filed on Jul. 20, 2012.

(51) Int. Cl.
*A61K 31/519* (2006.01)

(52) U.S. Cl.
CPC .................................. *A61K 31/519* (2013.01)

(58) Field of Classification Search
CPC ............................ A61K 31/571; A61K 31/519
See application file for complete search history.

(56) References Cited

U.S. PATENT DOCUMENTS

2002/0019526 A1 2/2002 Blumenkopf et al.

FOREIGN PATENT DOCUMENTS

WO 2010/020905 2/2010

OTHER PUBLICATIONS

PCT International Search Report, PCT/US2013/051015, mailed Aug. 29, 2013 (4 pages).

*Primary Examiner* — San-Ming Hui
(74) *Attorney, Agent, or Firm* — Paul M. Misiak

(57) ABSTRACT

The present invention provides a method for treating allergic dermatitis, atopic dermatitis, or one or more symptoms thereof in a mammal in need, which method comprises administering to the mammal a first therapeutically effective dose of a Janus Kinase (JAK) inhibitor twice a day for a number of days sufficient to ease or eliminate one or more clinical signs in the mammal, followed by a second therapeutically effective dose of the JAK inhibitor at a reduced frequency.

5 Claims, 2 Drawing Sheets

Notes:
1. Dose range of 0.6 mg/kg nominal dose was 0.6 to 0.701 mg/kg.
2. Dose range of 1.8 mg/kg nominal dose was 1.8 to 1.87 mg/kg.
3. Dose range of 3.0 mg/kg nominal dose was 3.0 to 3.06 mg/kg.
4. Time 0 plasma concentrations were used for 24 hour concentrations on study day 53 and 168.

DOSING REGIMEN FOR JANUS KINASE (JAK) INHIBITORS

FIELD OF THE INVENTION

This invention relates to Janus Kinase (JAK) inhibitors. This invention also relates to diseases and conditions such as itch, pruritus, and dermatitis. This invention also relates to the administration and dosing of certain compounds having activity as JAK inhibitors.

BACKGROUND OF THE INVENTION

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dys-regulation or de-regulation, as well as over- or under-production of growth factors or cytokines has been implicated in many diseases, including but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, survival, apoptosis, mitogenesis, cell cycle control, and cell mobility implicated in the aforementioned and related diseases.

Thus, protein kinases have emerged as an important class of enzymes as targets for therapeutic intervention. In particular, the JAK family of cellular protein tyrosine kinases (JAK-1, JAK-2, JAK-3, and Tyk-2) play a central role in cytokine signaling (Kisseleva et al, Gene, 2002, 285, 1; Yamaoka et al. Genome Biology 2004, 5, 253)). Upon binding to their receptors, cytokines activate JAK which then phosphorylate the cytokine receptor, thereby creating docking sites for signaling molecules, notably, members of the signal transducer and activator of transcription (STAT) family that ultimately lead to gene expression. Numerous cytokines are known to activate the JAK family.

SUMMARY OF THE INVENTION

The present invention provides a method for treating allergic dermatitis, atopic dermatitis, or one or more symptoms thereof in an animal, particularly a mammal in need, which method comprises administering to the mammal a first therapeutically effective dose of a Janus Kinase (JAK) inhibitor twice a day for a number of days sufficient to ease or eliminate one or more clinical signs in the mammal, followed by a second therapeutically effective dose of the JAK inhibitor at a reduced frequency.

In one embodiment, the first therapeutically effective dose and the second therapeutically effective dose are administered orally. In another embodiment, the first therapeutically effective dose is administered parenterally and the second therapeutically effective dose is administered orally.

The invention also provides a method for treating allergic dermatitis, atopic dermatitis, or one or more symptoms thereof in a mammal in need as described herein, wherein the JAK inhibitor is a compound of formula I:

or a pharmaceutically acceptable salt thereof, wherein $R^1$ is $C_{1-4}$ alkyl optionally substituted with hydroxyl. In one embodiment, $R^1$ is methyl. In another embodiment, $R^1$ is ethyl or cyclobutyl.

In another embodiment, the JAK inhibitor is N-methyl-1-{trans-4-[methyl(7H-pyrrolo[2,3-d]pyrimidin-4-yl)amino]cyclohexyl}methanesulfonamide, or a pharmaceutically acceptable salt thereof.

The invention also provides a method for treating atopic dermatitis or pruritus in a mammal in need comprising administering to the mammal a first therapeutically effective dose of N-methyl-1-{trans-4-[methyl(7H-pyrrolo[2,3-d]pyrimidin-4-yl)amino]cyclohexyl}methanesulfonamide, or a pharmaceutically acceptable salt thereof, orally, twice a day for a number of days sufficient to ease or eliminate one or more clinical signs in the mammal, followed by a second therapeutically effective dose, orally, of N-methyl-1-{trans-4-[methyl(7H-pyrrolo[2,3-d]pyrimidin-4-yl)amino]cyclohexyl}methanesulfonamide, or the pharmaceutically acceptable salt thereof at a reduced frequency.

In one embodiment of the invention, the mammal is a companion animal selected from a dog and a cat. In another embodiment, the mammal is a dog.

In one embodiment of the method of the invention for treating atopic dermatitis or pruritus in a mammal by administering a JAK inhibitor, for example N-methyl-1-{trans-4-[methyl(7H-pyrrolo[2,3-d]pyrimidin-4-yl)amino]cyclohexyl}methanesulfonamide, or a pharmaceutically acceptable salt thereof, the first therapeutically effective dose is from about 0.4 to about 0.6 mg/kg body weight of the mammal and is administered twice a day. In this embodiment, the second therapeutically effective dose is preferably from about 0.4 to about 0.6 mg/kg body weight of the mammal and is administered at the reduced frequency. In a further embodiment, the number of days of administration of the first therapeutically effective dose is from 1 day to 42 days, preferably 14 days.

This invention also provides method for treating a disease or condition caused by or associated with an immune system dysfunction or immune system dysregulation in a mammal in need, which method comprises orally administering to the mammal a therapeutically effective amount of a compound of formula I:

or a pharmaceutically acceptable salt thereof, wherein $R^1$ is $C_{1-4}$ alkyl optionally substituted with hydroxyl, two times per day for a period of from 1 day to 42 days (6 weeks), followed by administering to the mammal the therapeutically effective amount one time per day. Preferably, the compound is N-methyl-1-{trans-4-[methyl(7H-pyrrolo[2,3-d]pyrimidin-4-yl)amino]cyclohexyl}methanesulfonamide. Preferably, in this method, the therapeutically effective amount of the compound of formula I is administered to the mammal two times per day for a period of from 1 to 14 days, followed by administering to the mammal the therapeutically effective amount one time per day. In a further embodiment, the disease or condition is an allergic reaction or eczema.

The invention also provides for the method for treating a disease or condition caused by or associated with an immune system dysfunction or immune system dysregulation in a mammal in need as recited above, wherein the therapeutically effective amount of the compound of formula I is from about 0.4 mg/kg body weight of the mammal to about 3.0 mg/kg body weight of the mammal. The dose may be from 0.1 to 2 mg/kg, or 0.2 to 1 mg/kg, or 0.3 to 0.8 mg/kg. Preferably, the therapeutically effective amount of the compound of formula I is from about 0.4 mg/kg body weight of the mammal to about 0.6 mg/kg body weight of the mammal.

The invention also provides a method for improving the therapeutic ratio of a Janus Kinase-1 (JAK-1) inhibitor, comprising: administering to a mammal, over a period of at least 5-days, a plurality of therapeutically effective doses of said JAK-1 inhibitor sufficient to inhibit interleukins dependent on JAK-1; wherein the plurality of therapeutically effective doses do not reach peak drug levels of the JAK-1 inhibitor above the $IC_{50}$ for a hematopoietic cytokine. The invention further provides a method for maintaining the inhibition corridor in a mammal comprising administering the compound(s) described herein according to the dosing regimen described herein.

In a more particular embodiment, the interleukins are selected from the group consisting of IL-31, IL-4, IL-2, IL-6 and IL-13. In a more particular embodiment, the hematopoietic cytokines are selected from the group consisting of erythropoietin (EPO) or granulocyte colony-stimulating factor (GM-CSF). In another embodiment, the period of administration, is at least 10 days, 12 days, or preferably 14 days.

DETAILED DESCRIPTION

"Mammal" refers to humans or non-human animals, including livestock and companion animals. The phrase "companion animal" refers to an animal kept as a pet. Examples of companion animals include cats, dogs, and horses. The term "livestock" refers to animals reared or raised in an agricultural setting to make products such as food or fiber, or for its labor. In some embodiments, livestock are suitable for consumption by mammals, for example humans. Examples of livestock animals include cattle, goats, horses, pigs, sheep, including lambs, and rabbits. Also included within the definition of "mammal", for purposes of this invention, are birds, such as chickens, ducks and turkeys.

Figure 1:
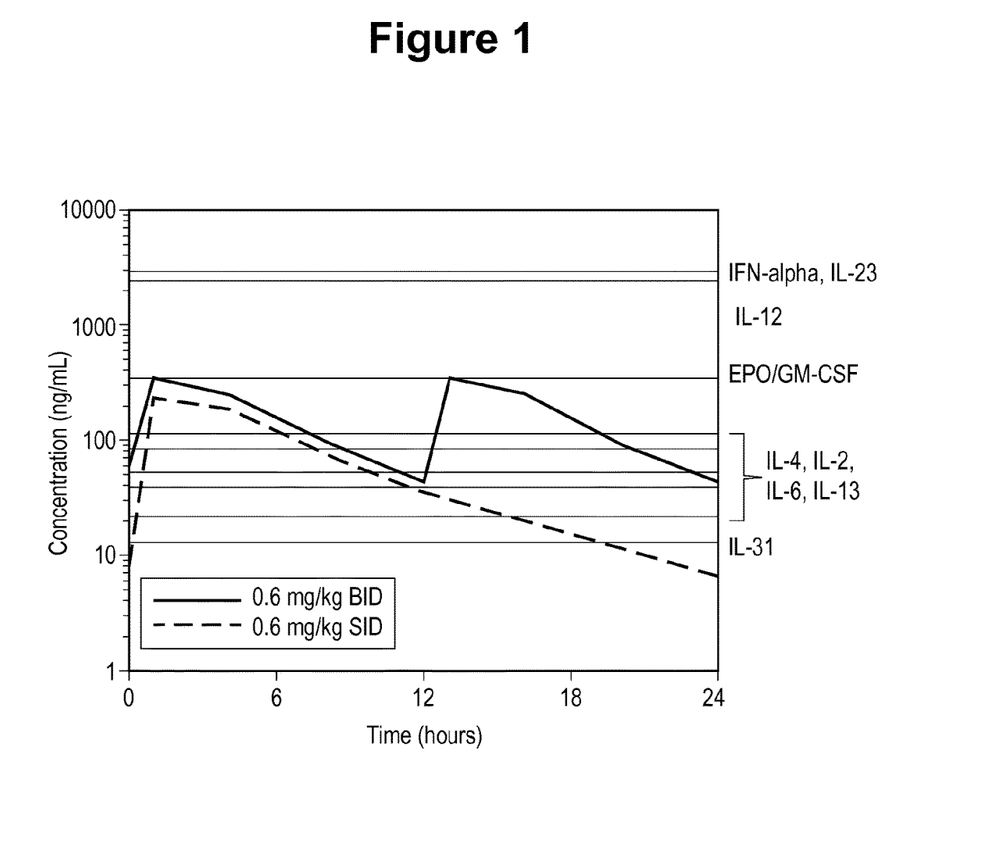
FIG. 1. Drug concentrations of Compound 1 and relationship to inhibition of cytokine function.
Figure 2:
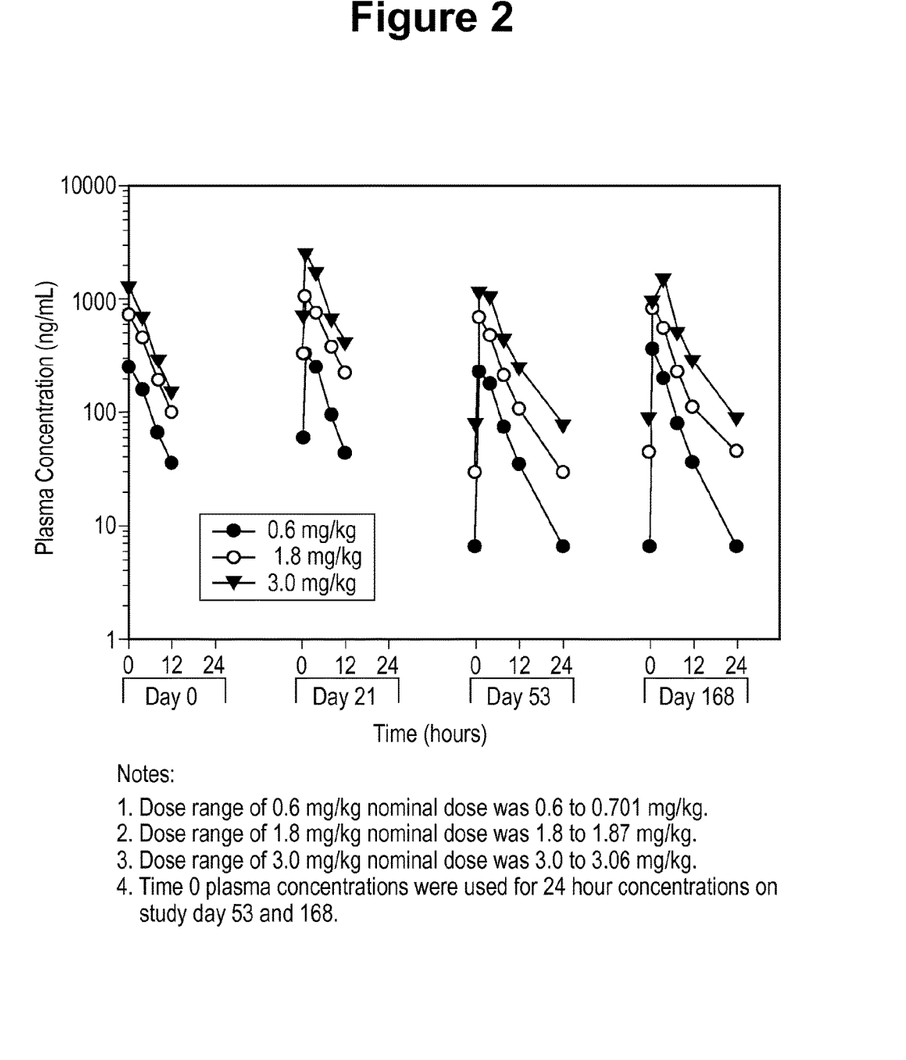
FIG. 2. Least-squares mean plasma concentration time profiles of Compound 1 in beagle dogs following oral twice daily administration (Day 0, 21) and once daily administration (Day 53, 168) of 0.6 mg/kg, 1.8 mg/kg and 3.0 mg/kg.

"Therapeutic ratio" as used herein refers to a comparison of the therapeutic effect to the toxicity or adverse effect of the drug. A therapeutic effect can be attained by reduction in the disease state or other forms of "treatment" as defined below. It can also be achieved by modulation of a particular target, such as inhibition of interleukins implicated in a disease state, such as atopic dermatitis. Accordingly, improving therapeutic ratio can occur by, for example, modifying the dosing regimen such that inhibition of interleukins associated with a target disease state occurs, while modulation of other cytokines associated with toxicity, such as EPO, GM-CSF, IL-12, IFN-alpha, or IL-23 is minimized, referred to herein as the "inhibition corridor". By carefully maintaining the inhibition corridor between toxic cytokines and efficacy-related cytokines (as depicted in FIG. 1), positive drug effects are maximized while minimizing or eliminating side-effect (i.e. improving the therapeutic ratio).

"Treating" or "treatment" as used herein means controlling, treating, or preventing the progression of the indicated condition or disease. The term "controlling", "treating" or "treatment" of a condition or disease includes: (1) preventing the condition or disease, i.e. causing the clinical symptoms or signs of the disease not to develop in a mammal that may be exposed to or predisposed to the disease but does not yet experience or display symptoms/signs of the disease; (2) inhibiting the disease, i.e., arresting or reducing the progression of the disease or its clinical symptoms or signs; or (3) relieving the disease, i.e., causing regression of the disease or its clinical symptoms or signs The JAK inhibitor is preferably a compound as described in US 2002/0019526 (Publication Date Feb. 14, 2002, from U.S. patent application Ser. No. 09/956,645, filed on Sep. 19, 2001), the teachings and contents of which are incorporated herein in their entirety by reference.

More preferably, the JAK inhibitor is a compound of formula I:

or a pharmaceutically acceptable salt thereof, wherein $R^1$ is $C_{1-4}$ alkyl optionally substituted with hydroxy. Compounds of formula I, their synthesis, and their use as JAK inhibitors are described in US 2010/0075996 A1 (Publication Date Mar. 25, 2010, from U.S. patent application Ser. No. 12/542,451, filed Aug. 17, 2009), the teachings and contents of which are hereby incorporated by reference in their entirety.

The "pharmaceutically acceptable salt" can be any salt suitable for pharmaceutical use in a mammal, preferably the acetate, ascorbate, aspartate, benzoate, besylate, bicarbonate/carbonate, bisulphate/sulphate, borate, camsylate, citrate, edisylate, etoglutarate, esylate, formate, fumarate, gluceptate, gluconate, glucuronate, glycerophosphate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate or trifluoroacetate salt. Preferably the pharmaceutically acceptable salt is the maleate (or maleic acid) salt.

Preferably the compound of formula I is N-methyl-1-{trans-4-[methyl(7H-pyrrolo[2,3-d]pyrimidin-4-yl)amino]cyclohexyl}methanesulfonamide or a pharmaceutically acceptable salt thereof. In a preferred embodiment, the compound of formula I is N-methyl-1-{trans-4-[methyl(7H-pyrrolo[2,3-d]pyrimidin-4-yl)amino]cyclohexyl}methanesulfonamide (referred to herein as compound 1), preferably the maleic acid salt The phrases "therapeutically effective amount" and "therapeutically effective dose" in general, unless otherwise specified, mean an amount of a compound that, when administered to a mammal for treating a condition or disease as recited, is sufficient to effect treatment of the condition or disease. More specifically, a therapeutically effective amount or dose means an amount of compound that, when administered according to a regimen as recited, is effective to prevent, alleviate or ameliorate symptoms or signs of a disease or condition or prolong the survival of the subject being treated. The "therapeutically effective amount" or "dose" may vary depending on the compound, the disease and its severity, and depending on the age, weight, and other such factors of the mammal to be treated.

Generally, a therapeutically effective amount of a JAK inhibitor for purposes of the present invention is from about 0.01 to about 100 mg/kg of body weight per day, preferably about 0.1 to about 10 mg/kg of body weight per day.

As described herein, the method for treating a disease or condition caused by or associated with an immune system dysfunction or dysregulation involves a first administration phase of a higher daily therapeutic dose to the mammal, followed by a second administration phase wherein the daily therapeutically effective dose of the JAK inhibitor is lower than the dose in the first phase. The daily therapeutically effective dose during the second administration phase can be at a reduced frequency relative to the dose during the first administration phase.

Preferably the "first therapeutically effective dose", which is the dose given during the first administration phase, is administered in divided doses, e.g. two times per day. Preferably the first therapeutically effective dose is, for example, from about 0.05 to about 3 mg/kg two times per day (BID), for a total daily dose of from about 1 mg/kg to about 6 mg/kg per day. More preferably, the first therapeutically effective dose is from about 0.1 to about 1 mg/kg BID, and even more preferably from about 0.4 to about 0.6 mg/kg BID. In another embodiment, the first therapeutically effective dose is from about 0.4 to about 3 mg/kg BID. In another embodiment, the first therapeutically effective dose is about 0.6 mg/kg, 1.8 mg/kg, or 3/0 mg/kg BID. In another embodiment, the first therapeutically effective dose is from about 0.2-0.3 mg/kg BID.

In one embodiment, the second therapeutic dose is the same as the first therapeutic dose, except that it is given at reduced frequency, for example one time per day (SID), relative to the frequency of the first therapeutic dose. In another embodiment, the second therapeutic dose is from about 0.05 to about 3 mg/kg one time per day (SID). More preferably, the second therapeutically effective dose is from about 0.1 to about 1 mg/kg SID, and even more preferably from about 0.4 to about 0.6 mg/kg SID. In another embodiment, the second therapeutically effective dose is from about 0.4 to about 3 mg/kg SID. In another embodiment, the second therapeutically effective dose is about 0.6 mg/kg, 1.8 mg/kg, or 3/0 mg/kg SID. In another embodiment, the second therapeutically effective dose is from about 0.2-0.3 mg/kg SID.

According to the method of the invention, the first therapeutically effective dose is given for a period of time, for example a number of days, sufficient to ease or eliminate one or more clinical signs of the disease or condition, for example the allergic dermatitis or atopic dermatitis. This can be conveniently referred to as a "first administration phase". The period of time sufficient to ease or eliminate one or more clinical signs of the disease or condition can be determined base on observation of reduction in the clinical sign or signs, for example using recognized criterion, as described in further detail herein. Thereafter, the period of time for the first administration phase can be set. In one embodiment, the first administration phase is from about 3 months. In another embodiment the first administration phase is 6 weeks, 4 weeks or 3 weeks. In another embodiment, the first administration phase is about 14 days. In another embodiment, the first administration phase is 10 days, 7 days, or 1, 2, 3, 4, 5, or 6 days.

Following the first administration phase, in the methods of the subject invention for treating a disorder or condition caused by, or associated with an immune system dysfunction or dysregulation, for example, atopic dermatitis or allergic dermatitis, a second therapeutically effective dose of the JAK inhibitor is administered to the mammal, and the second therapeutically effective dose is 1) a reduced daily dose relative to the daily dose of the first administration phase, and/or 2) a reduced frequency relative to the frequency of administration of the first therapeutically effective dose. As described, in one embodiment, the first therapeutic dose is BID and the second therapeutic dose is SID.

The route of administration for the first administration phase can be different from the route of administration for the second administration phase. For example, the route of administration for the first administration phase may be parenteral, and the route of administration for the second phase may be oral.

The term "clinical sign" as used herein refers to an observable or measureable condition or behavior in the mammal that is indicative of the disease, condition or symptom. Clinical signs may be those symptoms, conditions, or behaviors that are measured in known or established diagnostic assessments. For example, diagnostic assessments for a determination of allergic dermatitis or atopic dermatitis can be made by a Visual Analog Scale (VAS) Score or a clinical assessment of condition, or by an established scoring system such as the Canine Atopic Dermatitis Extent and Severity Index (CADESI) Score. Non-limiting examples of some clinical signs for atopic dermatitis and allergic dermatitis, that may be used sometimes in such assessments or scoring systems, include: itching, ranging from extremely severe (as demonstrated, in the case of a companion animal such as a dog, by scratching, chewing, licking almost continuously, regardless of what else is happening), to severe (as demonstrated by prolonged episodes of itching while awake, and itching at night and/or while eating, playing or exercising), to moderate (as demonstrated by frequent episodes of itching), to very mild (occasional episodes of itching); presence of pustules or epidermal collarets; presence of skin lesions; pruritus; erythema; erosions, excoriations and/or self-induced alopecia; presence of papules and/or crusts; lichenification and/or hyperpigmentation.

A "symptom" of a disease or condition is any of those symptoms known by a person of ordinary skill in the art as being associated with the disease or condition. In the case of atopic dermatitis, allergic dermatitis, flea allergy dermatitis, and sarcoptic mange, symptoms include, for example: pruritus, itch, and skin lesions.

In many cases, a "symptom" of a disease or condition, such as atopic dermatitis or allergic dermatitis is also a "clinical sign".

In the case of allergic dermatitis, the allergic dermatitis may be flea allergy dermatitis, i.e. "FAD" (also called "flea allergic dermatitis", "flea bite dermatitis" ("FBD"), or "flea-associated dermatitis), food allergy dermatitis, contact dermatitis, or allergic dermatitis associated with *Sarcoptes scabiei* (i.e. sarcoptic mange).

Other indications and conditions that can be treated by the methods including the dosing regimens described herein include any indications or conditions treatable by administration of a JAK inhibitor, including those involving Janus Kinase-1, Janus Kinase-2 or Janus Kinase-3. Such indications and conditions include organ transplant, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, leukemia, osteoarthritis, control of pruritus, chronic respiratory disease and other indications where immunosuppression or immunomodulation would be desirable.

The "administration" of the JAK inhibitor according to the methods described herein can be administration orally, parenterally, topically, rectally, transmucosally, or intestinally. Parenteral administrations include indirect injections to generate a systemic effect or direct injections to the afflicted area. Topical administrations include the treatment of skin or organs readily accessible by local application, for example, eyes or ears. It also includes transdermal delivery to generate a systemic effect. The rectal administration includes the form of suppositories. The preferred routes of administration are oral and parenteral, with oral being most preferred.

In the methods described herein, the JAK inhibitor can be administered in dosage forms corresponding to the selected route of administration. The pharmaceutical compositions of the JAK inhibitors can be formulated in conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991). The dosage form can be, for example, for oral administration: tablets or capsules prepared by conventional means with pharmaceutically acceptable excipients such as binding agents, fillers, lubricants or wetting agents; liquid preparations for oral administration such as solutions, syrups or suspension prepared by conventional means with conventional pharmaceutical excipients. For buccal administration, the dosage form may take the form of tablets or lozenges. The tablets may be chewable and/or flavored. For parenteral administration, the compositions may take such forms as suspensions, solutions or emulsions in oily or aqueous vehicles; or the JAK inhibitor may be in powder form for reconstitution or in concentrated liquid form for subsequent dilution before administration. Rectal dosage forms may be conventional suppositories or retention enemas. Topical forms may be ointments, salves or transdermal patches. The JAK inhibitor may also be in a dosage form suitable for intranasal administration, or administration by inhalation.

The following Examples illustrate the methods and dosing regimens of the invention, but they are not to be construed as limiting the invention as fully described in the specification and recited in the claims.

EXAMPLES

Pruritus Studies

A study was conducted in client owned dogs. Fifty-six dogs, greater than 1 year of age, weighing 2-50 kg, with a history of chronic atopic dermatitis were enrolled at three veterinary schools. The study design is illustrated in the following Table 1:

TABLE 1

| Treatment Group [1,2] | Treatment | Dose (mg/kg) | Regimen[3] | Route of Administration | Days of Study Visits[4] | Number of Dogs Enrolled |
|---|---|---|---|---|---|---|
| T01 | Placebo | 0.0 | BID for 28 days | Oral | 0, (7), 14, 28 | 29 |
| T02 | Compound 1[5] | 0.19-0.39 | BID for 28 days | Oral | 0, (7), 14, 28 | 27 |

[1] All site personnel were masked to treatment group assignment. Placebo capsules were identical in appearance to compound capsules
[2] Within each clinic, animals were blocked on order of enrollment with a block consisting of two animals
[3] +1 day [4]Telephone call [5]N-methyl-1-{trans-4-[methyl(7H-pyrrolo[2,3-d]pyrimidin-4-yl)amino]cyclohexyl}methanesulfonamide maleate The reduction in owner assessed VAS pruritus scores were significantly ($p \leq 0.07$) different for the compound-treated dogs compared with the placebo treated dogs at Day 1, 14 and 28. The reduction in investigator assessed CADESI-02 skin lesion scores were significantly ($p=0.272$) different for the compound-treated dogs compared to the placebo-treated.

In the following pruritus studies the owners had given consent and had completed a survey indicating that their dog exhibited moderate to severe itching. Investigators attributed pruritus to one or more of the following: allergic dermatitis, atopic dermatitis, food allergy, contact allergy, flea allergy, sarcoptic mange. Dogs were six months of age or older, weighed a minimum of 3 kg and were physically healthy apart from their pruritic condition. Dogs were flea-free, and appropriate preventatives and treatments were used throughout the studies.

The studies were designed as follows in Table 2 and Table 3.

TABLE 2

(Pruritus Study A)

| Treatment Group [1,2] | Treatment | Dose (mg/kg) | Regimen[3,4] | Route of Administration | Days of Study Visits[4] | Number of Dogs Enrolled |
|---|---|---|---|---|---|---|
| T01 | Placebo | 0.0 | BID for 7 days | Oral | 0, 7 | 220 |

TABLE 2-continued (Pruritus Study A)

| Treatment Group [1,2] | Treatment | Dose (mg/kg) | Regimen [3,4] | Route of Administration | Days of Study Visits [4] | Number of Dogs Enrolled |
|---|---|---|---|---|---|---|
| T02 | Compound 1 [5] | 0.4-0.6 | BID for 7 days | Oral | 0, 7 | 216 |

[1] All site personnel were masked to treatment group assignment. Placebo capsules were identical in appearance to compound capsules
[2] Within each clinic, animals were blocked on order of enrollment with a block consisting of two animals
[3] ±3 day [4] Treatment and Study Visits could continue through Day 28 ± 2 if underlying condition had not resolved
[5] N-methyl-1-{trans-4-[methyl(7H-pyrrolo[2,3-d]pyrimidin-4-yl)amino]cyclohexyl}methanesulfonamide maleate

TABLE 3

(Pruritus Study B)

| Treatment Group [1,2] | Treatment | Dose (mg/kg) | Regimen [3,4] | Route of Administration | Days of Study Visits [4] | Number of Dogs Enrolled |
|---|---|---|---|---|---|---|
| T01 | Prednisolone | 0.25-0.5 | BID for 14 days | Oral | 0, 7, 14 | 114 |
| T02 | Compound 1 [5] | 0.4-0.6 | BID for 14 days | Oral | 0, 7, 14 | 105 |

[1] The Owner and Veterinarian were masked to treatment group assignment. The Dispenser (technician) was not masked to treatment group assignment
[2] Within each clinic, animals were blocked on order of enrollment with a block consisting of two animals
[3] ±1 day [4] Treatment and Study Visits could be discontinued after Day 7 ± 1 if underlying condition had resolved
[5] N-methyl-1-{trans-4-[methyl(7H-pyrrolo[2,3-d]pyrimidin-4-yl)amino]cyclohexyl}methanesulfonamide maleate In the Pruritus Study A, the owner VAS scores by day were lower each day starting on day 1 for T02 compared to T01. By day 7, the LS mean VAS score was about 25 mm for T02, whereas for T01 (placebo), the LS mean VAS score was about 55 mm. Note, at time zero, the LS mean VAS score for both T01 and T02 was about 75 mm.

In the Pruritus Study B, the owner VAS scores over the 14 day period decreased for both T01 (prednisolone) and T02 (compound 1, i.e. N-methyl-1-{trans-4-[methyl(7H-pyrrolo[2,3-d]pyrimidin-4-yl)amino]cyclohexyl}methanesulfonamide maleate). At time point zero, both T01 and T02 had LS mean VAS scores of about 75 mm. At day 14, T01 has an LS mean VAS score of about 10 mm, and T02 has an LS mean VAS score of about 18 mm.

Atopic Dermatitis

In the following atopic dermatitis field studies, the owners had given consent and had completed a survey indicating that their dog exhibited either moderate to severe or mild to severe itching or dermatitis. Minimum CADESI scores were assigned by a dermatologist or veterinarian (CADESI-01 score of 25 or CADESI-3 score of 60). Dogs were either 1 year of age or 6 months of age or older and weighed a minimum of 3 kg and were physically healthy apart from their atopic disease. The dogs had at least a 1 year or 6 month documented history of chronic non-seasonal atopic dermatitis. The dogs were flea free and appropriate preventatives and treatments were used throughout the study.

Atopic Dermatitis "High Dose" Studies

In these studies, animals were administered from 0.4-0.6 mg/kg body weight of a JAK inhibitor BID for up to 112 days.

TABLE 4

| Study | Treatment Group [1,2] | Treatment | Dose (mg/kg) | Regimen | Route of Administration | Days of Study Visits [3,4] | Number of Dogs Enrolled |
|---|---|---|---|---|---|---|---|
| High Dose (BID) | T01 | Placebo | 0 | BID | Oral | 0, 14, 28, 56, 84, 112 | 170 |
| | T02 | Compound 1 [5] | 0.4-0.6 | BID | Oral | 0, 14, 28, 56, 84, 112 | 170 |

[1] All site personnel were masked to treatment group assignment. Placebo caplets were identical in appearance to compound caplets
[2] Within each clinic, animals were blocked on order of enrollment with a block consisting of four animals
[3] ±2-3 days [4] Dogs failing to show clinical improvement permitted to move into open-label (un-masked) study
[5] N-methyl-1-{trans-4-[methyl(7H-pyrrolo[2,3-d]pyrimidin-4-yl)amino]cyclohexyl}methanesulfonamide maleate

TABLE 5

| Study | Treatment Group [1,2] | Treatment | Dose (mg/kg) | Regimen | Route of Administration | Days of Study Visits [3,4] | Number of Dogs Enrolled |
|---|---|---|---|---|---|---|---|
| Positive Control | T01 | Atopica | 5 | Per Label | Oral | 0, 14, 28, 56, 84 | 132 |
| | T02 | Compound 1 [5] | 0.4-0.6 | BID | Oral | 0, 14, 28, 56, 84 | 138 |

[1] The Owner and Veterinarian were masked to treatment group assignment. The Dispenser (technician) was not masked to treatment group assignment
[2] Within each clinic, animals were blocked on order of enrollment with a block consisting of two animals
[3] ±2-7 days (depending on Study Visit) [4] Treatment and Study Visits could be discontinued at any time [5] N-methyl-1-{trans-4-[methyl(7H-pyrrolo[2,3-d]pyrimidin-4-yl)amino]cyclohexyl}methanesulfonamide maleate A dose regimen of 0.4-0.6 mg/kg BID showed excellent efficacy for the control of atopic dermatitis including pruritus and was safe for up to 90 to 112 days of treatment in client-owned dogs. This same regimen was safe for up to 90 days at elevated dosages. However, for long term administration, the BID dosing regimen could not be supported with an adequate margin of safety. Therefore, a dose selection study was conducted, as described below, to evaluate alternative dosing regimens.

A high dose (3 mg/kg BID) was given to 6 month old laboratory dogs. The dogs showed clinical signs of integument (7/8 dogs with demodex). At week 14, male dog showed pneumonia, peritonitis, pleuritis consistent with bacterial infection; lymphoid depletion; lymphadenitis; mild inflammation of choroid plexus and hepatitis. Female dog, at week 14, showed fever, demodex, pyoderma, and some pneumonia.

Although the 0.6 mg/kg BID group showed few effects, the bacterial and parasitic infection in the 3 mg/kg BID dose group did not support chronic use BID.

Atopic Dermatitis Dose Selection Study

TABLE 6

Atopic Dermatitis Dose Selection Study

| Treatment Group [1,2] | Treatment | Dose (mg/kg) | Regimen | Route of Administration | Days of Study Visits [3,4] | Number of Dogs Enrolled |
|---|---|---|---|---|---|---|
| T01 | Placebo | 0.0 | BID for 14 days | Oral | 0, 14, 28, 56, 84, 112 | 54 |

TABLE 6-continued

Atopic Dermatitis Dose Selection Study

| Treatment Group[1,2] | Treatment | Dose (mg/kg) | Regimen | Route of Administration | Days of Study Visits[3,4] | Number of Dogs Enrolled |
|---|---|---|---|---|---|---|
| T02 | Compound 1[5] | 0.4-0.6 | followed by SID thereafter BID for 14 days followed by SID thereafter | Oral | 0, 14, 28, 56, 84, 112 | 59 |
| T03 | Compound 1[5] | 0.4-0.6 | SID[6] | Oral | 0, 14, 28, 56, 84, 112 | 52 |
| T04 | Compound 1[5] | 0.2-0.3 | SID[6] | Oral | 0, 14, 28, 56, 84, 112 | 55 |

[1]All site personnel were masked to treatment group assignment. Placebo caplets were identical in appearance to compound 1 caplets
[2]Within each clinic, animals were blocked on order of enrollment with a block consisting of four animals
[3]±2 days
[4]Dogs failing to show clinical improvement permitted to move into open-label (unmasked) study
[5]N-methyl-1-{trans-4-[methyl(7H-pyrrolo[2,3-d]pyrimidin-4-yl)amino]cyclohexyl}methanesulfonamide maleate
[6]With placebo administered SID for first 14 days to ensure masking Owner VAS scores for atopic dermatitis over the 112 days of study were in the following order from highest VAS score (most atopic dermatitis) to lowest VAS score: T01, T04, T03, and T02. Investigator CADESI score over the 112 days of study were in the following order from highest CADESI score (highest demonstration of atopic dermatitis) to lowest CADESI score: T01 (placebo), T04 (0.2-0.3 mg/kg SID compound 1), T03 (0.4-0.6 mg/kg SID compound 1), and T02 (0.4-0.6 mg/kg BID for 14 days followed by 0.4-0.6 mg/kg SID thereafter).

Target Animal Safety Studies

A target animal safety program (8 studies) was conducted. 131 laboratory-bred dogs were exposed to N-methyl-1-{trans-4-[methyl(7H-pyrrolo[2,3-d]pyrimidin-4-yl)amino]cyclohexyl}methanesulfonamide maleate (i.e. N-methyl-1-{trans-4-[methyl(7H-pyrrolo[2,3-d]pyrimidin-4-yl)amino]cyclohexyl}methanesulfonamide maleic acid salt maleic acid salt). Doses ranged from 0.5 mg/kg/day (0.25 mg/kg BID) to 18 mg/kg/day (9 mg/kg BID). Duration of exposure ranged from 10 days to 6 months. Recovery periods were incorporated into two studies. A series of early studies were designed to ensure the safety of client-owned dogs in the field safety and efficacy studies.

In a "margin of safety" study, the following treatments were given:

| Treatment | Number of Animals[1] (M/F) | Dose (oral) | Regimen Weeks 1-6 | Regimen Weeks 7-26 | Dosing Days |
|---|---|---|---|---|---|
| T01 | 4/4 | 0.0 mg/kg | 2 per day | 1 per day | 180 |
| T02 | 4/4 | 0.6 mg/kg | 2 per day | 1 per day | 180 |
| T03 | 4/4 | 1.8 mg/kg | 2 per day | 1 per day | 180 |
| T04 | 4/4 | 3.0 mg/kg | 2 per day | 1 per day | 180 |

Results of the "margin of safety" study were no observed deaths or other serious adverse events. Test article and dose related clinical signs were primarily seen grossly in the exacerbation of interdigital furunculosis with associated peripheral lymphadenopathy and the occasional development of papillomas. From this study, we concluded oral administration of N-methyl-1-{trans-4-[methyl(7H-pyrrolo[2,3-d]pyrimidin-4-yl)amino]cyclohexyl}methanesulfonamide in dogs, BID for 6 weeks followed by SID (one time per day) for 20 weeks at 0.6, 1.8, or 3.0 mg/kg for a total of 26 weeks (6 months) was well tolerated at all dose multiples. The test article effects in all groups were consistent with the pharmacological action of the drug class, and most effects were mild and non-progressive. Chronic use is supported in the population of dogs greater than 1 year old.

Results and Discussion

Any immune modulator may increase susceptibility to infections (dose dependent). Bacterial and fungal infections of the skin were the most common type of infection reported in dogs in the field safety and efficacy studies; these responded to appropriate antimicrobial therapy. In a high dose target animal safety study, in dogs less than one year old, at elevated doses, parasitic infestations (demodicosis) and pneumonia were observed. Demodicosis was reported in two dogs and pneumonia (attributable to a pulmonary mass) on one dog in the field safety and efficacy studies.

In summary, in the control or treatment of pruritus associated with allergic dermatitis and the control of atopic dermatitis in dogs, using a JAK inhibitor, N-methyl-1-{trans-4-[methyl(7H-pyrrolo[2,3-d]pyrimidin-4-yl)amino]cyclohexyl}methanesulfonamide maleate, a dosing regimen of 0.4-0.6 mg/kg BID for 14 days followed by SID thereafter is supported. The target animal safety studies support the long-term and chronic administration of N-methyl-1-{trans-4-[methyl(7H-pyrrolo[2,3-d]pyrimidin-4-yl)amino]cyclohexyl}methanesulfonamide maleate in dogs.

Pharmacokinetic and Pharmacodynamic Studies:

A. Pharmacokinetic Studies

N-methyl-1-{trans-4-[methyl(7H-pyrrolo[2,3-d]pyrimidin-4-yl)amino]cyclohexyl}methanesulfonamide has been studied as the maleate salt (N-methyl-1-{trans-4-[methyl(7H-pyrrolo[2,3-d]pyrimidin-4-yl)amino]cyclohexyl}methanesulfonamide maleate), hereinafter Compound 1. All doses are expressed in terms of mg/kg of free base. Serial blood samples for determination of pharmacokinetics were collected following Compound 1 administration. Blood samples at 0, 1, 4, 8, and 12 hours post dose were collected via jugular venipuncture into $K_2EDTA$ tubes and placed on ice until centrifuged. Harvested plasma was stored at approximately −20° C. until analysis.

Thirty-two beagle dogs (16 female, 16 male) were allocated to four treatment groups. Dogs in Treatment 1 received placebo capsule (0 mg/kg) orally. Dogs in Treatments 2, 3 and 4 received a combination of whole and half 3.6, 5.4, and 16 mg sized tablets orally to result in target doses of 0.6, 1.8 and 3.0 mg/kg, respectively. All dogs received a twice daily doses 0, 0.6, 1.8, and 3.0 mg/kg for weeks 1 through 6 and a single daily doses of 0, 0.6, 1.8, and 3.0 mg/kg for weeks 7 through 26. On pharmacokinetic sample collection days, dogs were fasted the previous night and fed four hours post dose administration. To calculate $AUC_{0-24}$ for study days 53 and 168, steady-state was assumed and the 24 hour concentration was assumed to be equal to the 0 hour concentration, and used for the 0 hour concentration. As the actual doses of Compound 1 varied from the group target doses, the pharmacokinetic variables $AUC_{0-\tau}$, (AUC of the dosing interval), $C_{max}$, and $C_\tau$ (trough concentration) were all normalized to the group target dose.

On Day 0, $AUC_{0-12}$ and $C_{max}$ increased in a dose related manner following oral administration of tablets dosed at target doses of 0.6 mg/kg, 1.8 mg/kg and 3.0 mg/kg. The increase in $AUC_{0-12}$ and $C_{max}$ was dose proportional from 0.6 to 3.0 mg/kg.

Across all days and doses, there did not appear to be any systematic male/female differences in pharmacokinetic parameters. Plasma exposure increased with the number of doses following twice a day administration with a significant difference at the 0.10 level in $AUC_{0-12}$ for study Day 0 in comparison to Day 21. There was a numerical decrease in the plasma exposure over the 24 hour period following the change in dosing regimen to once a day on Day 43. The Day 0 and Day 53 least-squares mean values for $C_{max}$ were not significantly different for 0.6, 1.8, and 3.0 mg/kg. Day 53 and Day 168 the least-squares mean values for $C_{max}$ and $AUC_{0-24}$ were not significantly different for 1.8 and 3.0 mg/kg. While the Day 53 and Day 168 least-squares mean values for $C_{max}$ and $AUC_{0-24}$ following 0.6 mg/kg once a day were significantly different, the $C_T$ values were not.

Other pharmacokinetic studies were completed that demonstrated following oral administration, Compound 1 was rapidly absorbed in dogs with mean maximum plasma concentrations occurring at approximately 1 hour post dose. This absorption is consistent with the observed rapid onset of pruritus reduction in both laboratory and field studies (Cosgrove, Wren et al. 2012; Fleck, Humphrey et al. 2012). Compound 1 is a low clearance compound with a moderate volume of distribution. The absolute oral bioavailability was high with a mean range of 79% to 89%. Furthermore, it can be concluded that the absorption is nearly complete based on the calculated fraction absorbed of greater than 0.9 (based on bioavailability of 85%, mean clearance of 4 mL/min/kg, and blood flow of 40 mL/min/kg). The observed increase in mean $AUC_{0-12}$ from Day 0 to Day 21 of 40% was slightly greater than the expected increase of approximately 15% based on plasma elimination half-life (t½) of 4 hours. Though assuming a t½ of 4 hours, it would be predicted that steady state would be achieved by the second dose following the dose regimen change from twice daily to once daily. The similarity of the observed pharmacokinetic parameters on Day 53 (change from twice a day to once a day was on day 43) and Day 168 at 0.6 mg/kg once a day supports this conclusion.

The observed pharmacokinetic parameters of rapid oral absorption and high bioavailability are consistent with the physicochemical properties of Compound 1. The in vitro permeability of Compound 1 was experimentally determined in a Caco-2 cell monolayer study. The permeability was high, $40.4 \times 10^{-6}$ cm/sec, greater than the control for high permeability (Pfizer internal data not shown). Additionally, the solubility of Compound 1 is pH dependent with a significant drop in solubility above pH 4 down to practically insoluble by pH 5.5. The dog gastric pH has been reported to range from 1.08 to 2.0 (Sagawa, Li et al. 2009; Mahar, Portelli et al. 2012). At this pH range and the solubility of Compound 1 (10.43 mg/mL at pH3.8) the dose for a 10 kg dog (6 mg) would fully dissolve 0.6 mL. Though the estimation of the liquid volume to use for a dog is complex due to the relative small number of studies in the literature, the large size differences among individual dogs and the lack of administration of water with doses, the suggested volumes for a 10 kg dog of 9 to 20 mL are well above what is needed for Compound 1 to be fully soluble (Martinez and Papich 2012). The solubility profile of Compound 1 is also supportive of the lack of a prandial effect. Though the pH in the fed state has been shown to spike to around pH 7, a majority of the time the pH is 2 to 4. Thus, under these conditions, Compound 1 is expected to be fully dissolved in both states, furthering supporting the observed experimental result that Compound 1, given with or without food results in a similar oral pharmacokinetic profile. This result of similar pharmacokinetics is important for ease of administration by pet owners because dosing time does not have to be considered in respect to feed time like other AD treatments in dog.

The plasma concentration time profiles and the pharmacokinetic parameters following IV and PO administration to beagle and mongrel dogs were very similar. Although a statistical test for equivalence was not performed due to the inability to randomize beagles and mongrels between rooms, the similarity of the means and the overlap of the confidence intervals following both IV and oral administration leads to the conclusion that breed does not impact the pharmacokinetic profile. Though a formal population model was not developed all the pharmacokinetic data predicts that no clinically different pharmacokinetic profiles in client-owned dog would be different from those reported here.

The pharmacokinetic studies demonstrate that at the dose of 0.4 to 0.6 mg/kg Compound 1 exhibits rapid and nearly complete absorption, low clearance, no pharmacokinetic differences in male, female, fed, fasted, beagle and mongrel dogs, and dose proportionality. These pharmacokinetic properties are ideal for a daily or twice-daily orally administered product for the control of pruritus associated with allergic dermatitis and control of atopic dermatitis.

B. Pharmacodynamic Studies:

The relationship of drug levels to pharmacodynamic effects (inhibition of cytokine function) is another factor that is important to consider when assessing potential effects of inhibiting Janus kinases. Compound 1 is a reversible inhibitor, and there is a direct relationship with drug levels and inhibition of cytokine function. Therefore, when drug levels reach $IC_{50}$ levels or higher, there is a potential to significantly inhibit the function of certain cytokines, either favorably in terms of efficacy or unfavorably in terms of safety. Drug levels seen at the 0.6 mg/kg dose of compound 1 given either twice daily or once daily are shown in FIG. 1.

Compound 1 inhibits cytokine receptors that share the common gamma chain (e.g. IL-2R, IL-4R), since $IC_{50}$'s of representative family members range from 63-249 nM or 21-84 ng/mL, and drug levels reach those levels or higher for a significant period of time after dosing. Compound 1 also inhibits the function of a variety of cytokine receptors that share the gp130 subunit (e.g. IL-6) as well as IL-13. And finally, although not wishing to be bound by a theory, it is possible that compound 1 inhibits the function of Type I and II interferons based on the JAKs that are used by its receptor for signaling (see FIG. 1). However, it does not appear that compound 1 inhibits cytokines from the—the IL-10 family, the IL-12 family (that share the p40 subunit), or the IL-3 family. Additionally, hormone receptors that utilize JAK2 are not substantially inhibited since drug levels do not get above $IC_{50}$'s for other related receptor systems utilizing JAK2 exclusively for signaling (FIG. 1).

Collective knowledge of cytokine biology, cell types that may express JAK-dependent cytokine receptors as well as potency of compound 1 toward various classes of JAK-dependent cytokine receptors were used to help identify potential preferred dosing regimen of compound 1 (see FIG. 1). A variety of assessments were incorporated into the dosing study to evaluate the potential for any of the identified risks as well as unanticipated risks that our Janus kinase inhibitor, compound 1, may pose to the animal. These were contrasted with the need for adequate drug to impart efficacy.

Laboratory data supporting the identifying dosing regimen included: 1) inhibition ($IC_{50}$'s less than 249 nM or 84 ng/mL) of JAK-1 dependent cytokines (e.g. IL-2, IL-4, IL-6, IL-13, and IL-31) and the ability to achieve drug levels that will inhibit these cytokines with the twice daily or once daily dosing regimen at the recommended use dose, 2) $IC_{50}$'s for cytokines that are exclusively dependent on JAK2 function (EPO, GM-CSF) are 4-17-fold less potent than the JAK1-dependent cytokines evaluated and involved in allergic skin disease (IL-2, 4, 6, 13, and 31), 3) $IC_{50}$'s for other cytokines that utilize JAK2/TYK2 and not JAK1 (IL-12 and IL-23) are greater than 3000 nM (IL-12, IL-23), 4) peak drug levels (973 nM or 328 ng/mL) observed in the margin of safety study (0.6 mg/kg dose) do not reach above the $IC_{50}$'s for any of the cytokines dependent on JAK2 (EPO, GM-CSF, IL-12, IL-23), and 4) significant decreases in red blood cell parameters that fall outside of normal laboratory reference ranges were not detected at the 0.6 mg/kg dose when evaluated.

The plasma concentrations that are achieved following the efficacious dose of 0.4 to 0.6 mg/kg are thought to balance safety and efficacy. The observed plasma concentrations following the twice a day regimen resulted in plasma concentrations that are greater than the JAK-1 dependent cytokine inhibitory concentrations for the entire dosing regimen. Thus, in order to fall within the preferred inhibition corridor, Compound 1 was not constantly administered twice daily for chronic use. Twice daily dosing for the first 14 days of treatment is intended to rapidly safely and effectively break the itch scratch cycle, and down-regulate the inflammatory, allergic and pruritogenic cytokine activity. Subsequent once daily dosing provides a solid margin of safety while maintaining efficacy for chronic use.

What is claimed is:

1. A method for treating allergic dermatitis, atopic dermatitis, or one or more symptoms thereof in a dog in need, which method comprises administering to a dog a first therapeutically effective dose of the Janus Kinase (JAK) inhibitor, N-methyl-1-{trans-4-[methyl(7H-pyrrolo[2,3-d]pyrimidin-4-yl)amino]cyclohexyl}-methanesulfonamide, or a pharmaceutically acceptable salt thereof, twice a day for up to 14 days, to ease or eliminate one or more clinical signs in the dog, followed by a second therapeutically effective dose of the JAK inhibitor at a reduced frequency of once a day.

2. The method according to claim 1 for treating pruritus associated with allergic dermatitis or pruritus associated with atopic dermatitis.

3. The method according to claim 1 wherein the first therapeutically effective dose and the second therapeutically effective dose are administered orally.

4. The method according to claim 1, wherein the first therapeutically effective dose is from about 0.4 to about 0.6 mg/kg body weight of the dog.

5. The method according to claim 1, wherein the second therapeutically effective dose is from about 0.4 to about 0.6 mg/kg body weight of the dog.

* * * * *